United States Patent [19]
Katayama et al.

[11] Patent Number: 5,552,612
[45] Date of Patent: Sep. 3, 1996

[54] TRANSPORT CONTAINER FOR TRANSPORTING RADIATION SHIELD MEMBER

[75] Inventors: Hitoshi Katayama; Noboru Minamiguchi; Yoshimasa Tanaka, all of Sanda, Japan

[73] Assignee: Nihon Medi-Physics Co., Ltd., Nishinomiya, Japan

[21] Appl. No.: 362,161

[22] Filed: Dec. 22, 1994

[30] Foreign Application Priority Data

Dec. 29, 1993 [JP] Japan .................. 5-349636

[51] Int. Cl.$^6$ .................................. G21F 5/00
[52] U.S. Cl. ........................................ 250/506.1
[58] Field of Search ................. 250/506.1, 507.1; 376/272, 287, 263

[56] References Cited

U.S. PATENT DOCUMENTS

| | | | |
|---|---|---|---|
| 3,256,441 | 6/1966 | Grasty | 250/506.1 |
| 3,531,644 | 9/1970 | Koster et al. | 250/506.1 |
| 3,769,490 | 10/1973 | Czaplinski | 250/506.1 |
| 4,788,438 | 11/1988 | Evers | 250/506.1 |
| 4,846,235 | 7/1989 | Handke | 250/506.1 |
| 4,886,497 | 12/1989 | Scholl | 604/111 |
| 4,923,088 | 5/1990 | Tanaka et al. | 220/468 |
| 5,417,326 | 5/1995 | Winer | 206/365 |

FOREIGN PATENT DOCUMENTS

| | | |
|---|---|---|
| 55-170262 | 12/1980 | Japan . |
| 2-95380 | 4/1990 | Japan . |
| 5-24078 | 6/1993 | Japan . |

Primary Examiner—Bruce C. Anderson
Attorney, Agent, or Firm—Jones, Tullar & Cooper, P.C.

[57] ABSTRACT

A transport container for transporting a radiation shield member which is light and capable of preventing a radiation shield member from popping out from the transport container by accident. The container has a favorable operability, and is capable of easily separating a reusable portion and a portion other than the reusable portion. The transport container includes a cup-shaped sheath container, a radiation shield container accommodated in the sheath container and having concaves recesses, formed thereon, engaging wing-shaped holding members of the radiation shield member, a holding frame, mounted on the sheath container, for preventing the radiation shield container and the radiation shield member from being removed from the transport container, and a cover for closing the opening end of the sheath container.

13 Claims, 14 Drawing Sheets

TRANSPORT CONTAINER FOR TRANSPORTING RADIATION SHIELD MEMBER

BACKGROUND OF THE INVENTION

The present invention relates to a transport container for transporting a radiation shield member in which a syringe containing a radiopharmaceutical liquid is mounted.

As a transport container for transporting a syringe in which radiopharmaceutical liquid has been filled, a container as disclosed in Japanese Laid-Open Patent Publication No. 2-95380 is known. In the container disclosed in the Patent publication, a shield material made of lead is provided along the inner peripheral surface of the container to prevent radiation emitted from a syringe, containing radiopharmaceutical liquid, accommodated therein from leaking to the outside thereof. Further, in the container, a cushioning material such as styrene foam conforming to the outer configuration of the syringe containing the radiopharmaceutical liquid is provided between the shield material and the syringe containing the radiopharmaceutical liquid so as to fix the syringe in the container. Thus, the outer diameter of the container is large and hence the outer diameter of the shield material is also large. Accordingly, the container disclosed in the Patent Publication has a disadvantage that the weight of the container is large.

The above-described container has another disadvantage in that because the container does not have a mechanism for fixing the shield material and the container made of plastic to each other, it is necessary to bond them to each other with an adhesive double coated tape or the like and thus it is uneasy to separate plastic and lead from each other for classified refuse.

Further, the container has another disadvantage that because the syringe containing the radiopharmaceutical liquid is held in the container by pressing the syringe into the shield material, the syringe accommodated in the container is popped out therefrom and the syringe containing the radiopharmaceutical liquid is damaged if the container upsets or is inclined by accident with the cover of the container open.

The cover made of plastic is fitted on the opening of the container and a shield material of a lead plate is provided in the cover to shield the radiation emitted from the syringe containing the radiopharmaceutical liquid. But the shield material formed on the cover is not bonded to the inner peripheral surface of the cover of the container, and thus it is necessary to remove the shield material provided in the cover from the container after the cover is opened. Thus, the container has still another disadvantage that its operability is bad.

Furthermore, since the cover has little play, an operator may have difficulty to some degree in opening and closing the cover. Thus, the operability of the container is bad.

SUMMARY OF THE INVENTION

Accordingly, an object of the present invention is to provide a transport container, for transporting a radiation shield member, which is light in weight and has a favorable operability.

In accomplishing this object, according to a first aspect of the present invention, there is provided a transport container for accommodating a radiation shield member accommodating a syringe having radiopharmaceutical liquid filled thereinto and having a wing-shaped holding member at an opening end thereof, the transport container comprising:

a cup-shaped sheath container for accommodating the radiation shield member and having a first engaging portion formed on an outer peripheral surface thereof in a vicinity of an opening end thereof;

a cup-shaped radiation shield container made of radiation shield material, having a predetermined thickness, an outer peripheral surface of a side wall thereof which substantially contacts an inner peripheral surface of the sheath container, and having a position-fixing portion, for fixing the wing-shaped holding member, to be engaged by the wing-shaped holding member at an opening end thereof; and a cup-shaped cover mounted on the opening end of the sheath container, having a cup-shaped radiation shield member made of radiation shield material and held therein, and having a second engaging portion which engages the first engaging portion of the sheath container, thus closing an opening of the sheath container by engagement between the first engaging portion and the second engaging portion.

According to a second aspect of the present invention, there is provided the transport container for accommodating the radiation shield member, further comprising a holding frame including:

a portion having a frame-shaped sectional configuration and a size appropriate for contacting the inner peripheral surface of the sheath container in the vicinity of the opening end thereof;

a shield container removal-preventing portion extending from the frame-shaped sectional portion toward a center of the frame-shaped sectional portion in contact with an end surface of the opening end of the radiation shield container, thus preventing the radiation shield container from being removed from the sheath container; and a shield member removal-preventing portion extending from the shield container removal-preventing portion so as to cover the wing-shaped holding member engaged with the position-fixing portion for fixing the wing-shaped holding member, thus preventing the radiation shield member from being removed from the radiation shield container.

According to a third aspect of the present invention, there is provided a transport container for accommodating the radiation shield member, wherein the cover has a fifth engaging portion on an inner peripheral surface of a side wall thereof; and the cup-shaped radiation shield member formed on the cover has a height smaller than a depth of the cover, having a side wall, an outer side of which is opposed to an inner peripheral surface of a side wall of the cover with a gap provided therebetween, and having on an outer peripheral surface of the side wall thereof a sixth engaging portion engaging the fifth engaging portion, thus removably holding the cup-shaped radiation shield member on the cover.

BRIEF DESCRIPTION OF THE DRAWINGS

These and other objects and features of the present invention will become clear from the following description taken in conjunction with the preferred embodiments thereof with reference to the accompanying drawings, in which:

FIG. 12 is a perspective view showing the radiation shield member and the like;

DETAILED DESCRIPTION OF THE EMBODIMENTS

Figure 1:
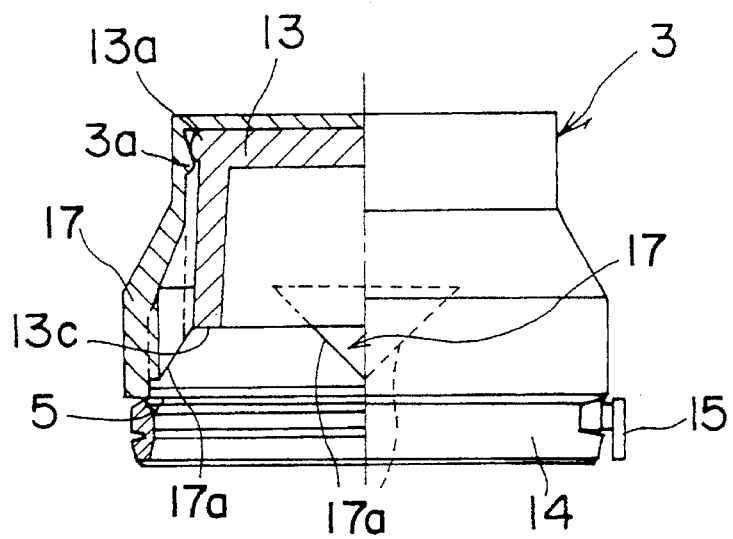
FIG. 1 is a view showing a cover constituting a container for transporting a radiation shield member according to an embodiment of the present invention, in which the left side with respect to a center axis is a sectional view of the cover, and the right side with respect to the center axis is a front view thereof.

Before the description of the present invention proceeds, it is to be noted that like parts are designated by like reference numerals throughout the accompanying drawings.

Containers for transporting radiation shield members according to embodiments of the present invention are described below with reference to the drawings.

Figure 3:
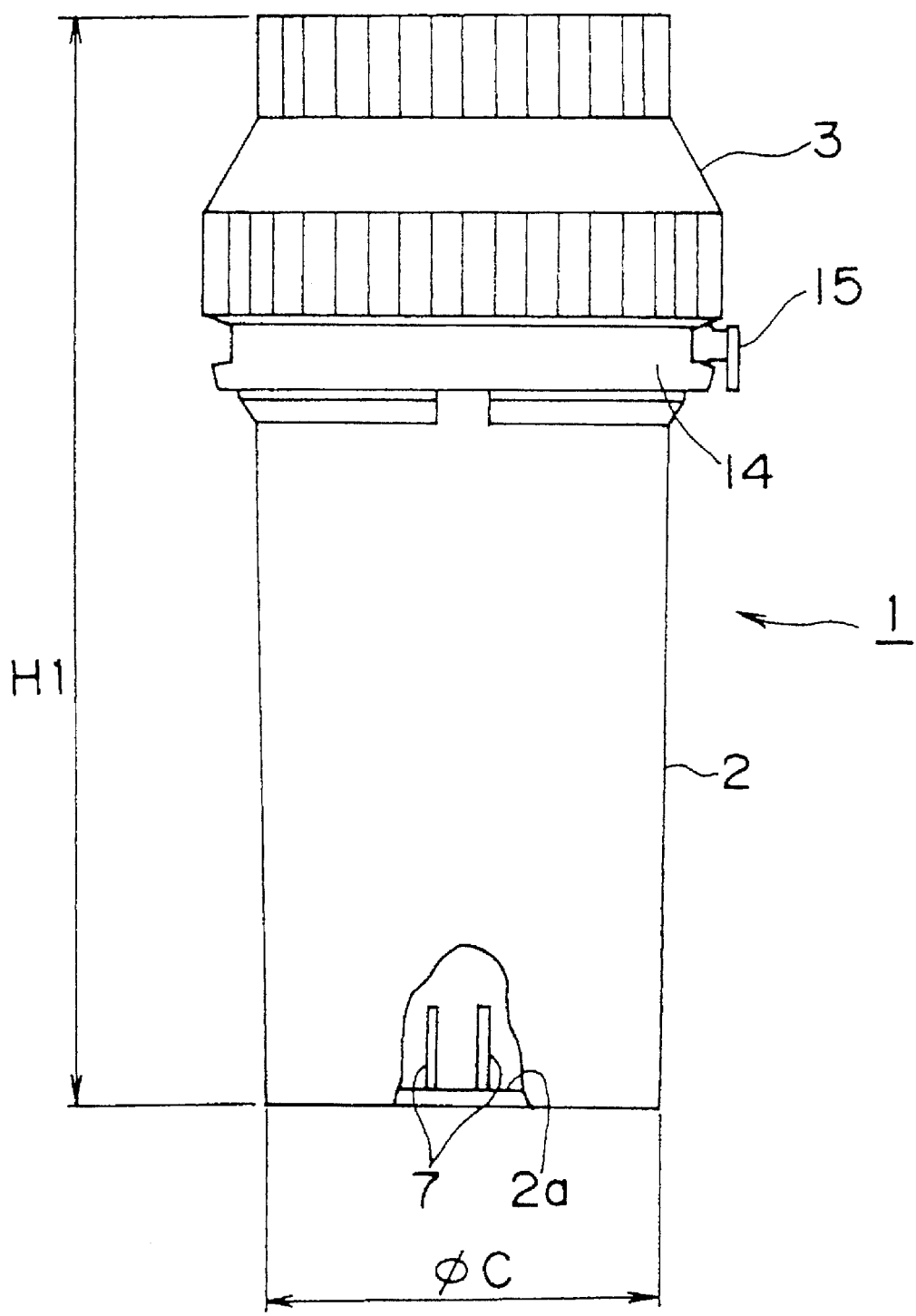
FIG. 3 is a partially-broken view showing an outer configuration of the container for transporting the radiation shield member according to an embodiment of the present invention.

A transport container 1 for transporting a radiation shield member according to an embodiment of the present invention is cylindrical as shown in FIG. 3, and is 37 mm in its diameter (C) and approximately 106 mm in its height (H1). The transport container 1 for transporting a radiation shield member comprises a sheath container 2 cup-shaped and made of plastic; and a cover 3, cup-shaped and made of plastic, covering an opening of the sheath container 2, thus closing the opening end thereof. The cover 3 has a sealing mechanism which is unrestorable when the cover 3 is removed from the sheath container 2. The sealing mechanism will be described later in detail.

Figure 12:
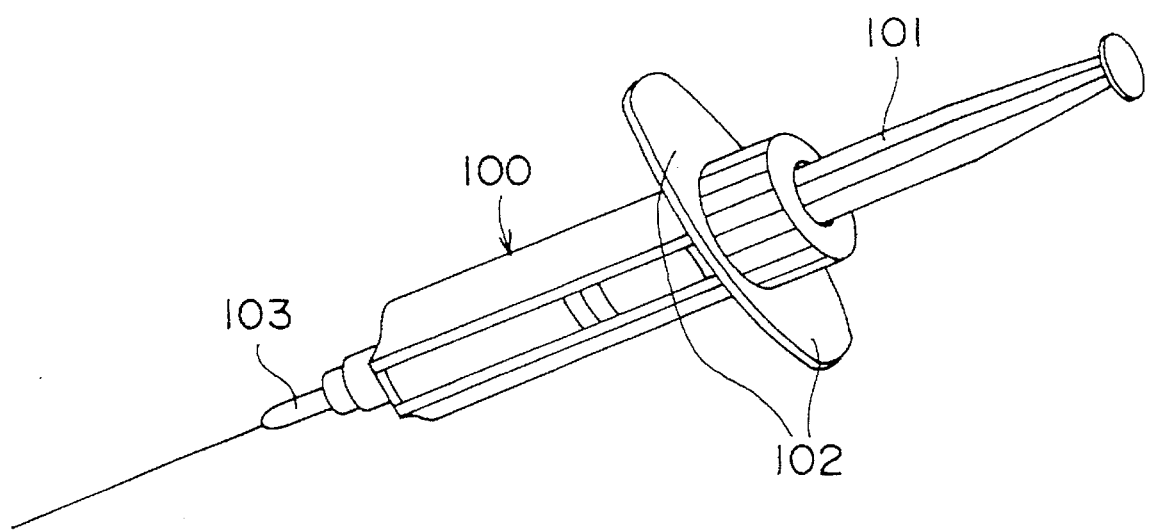

The transport container 1 for transporting the radiation shield member according to the embodiment accommodates in the sheath container 2 a first radiation shield member 100 having a syringe, in which radiopharmaceutical liquid is filled, inserted thereinto as shown in FIG. 12. The radiation shield member 100 to be accommodated in the sheath container 2 containing the syringe has been on the market. Two wing-shaped holding members 102 extending in opposed directions to each other in a diametrical direction of the syringe and perpendicular to the axial direction of the syringe is formed on one side of the radiation shield member 100 from which a plunger 101 connected with a gasket provided in the syringe projects. When the radiation shield member 100 shown in FIG. 12 is accommodated in the transport container 1 for transporting the radiation shield member 100, the radiation shield member 100 does not have the plunger 101 or a needle 103 mounted thereon, but a radiation shield member having a plunger mounted thereon may be accommodated in the transport container 1 for transporting the radiation shield member. In this case, needless to say, a cover is formed in conformity to the length of the plunger and the configuration thereof.

Figure 2:
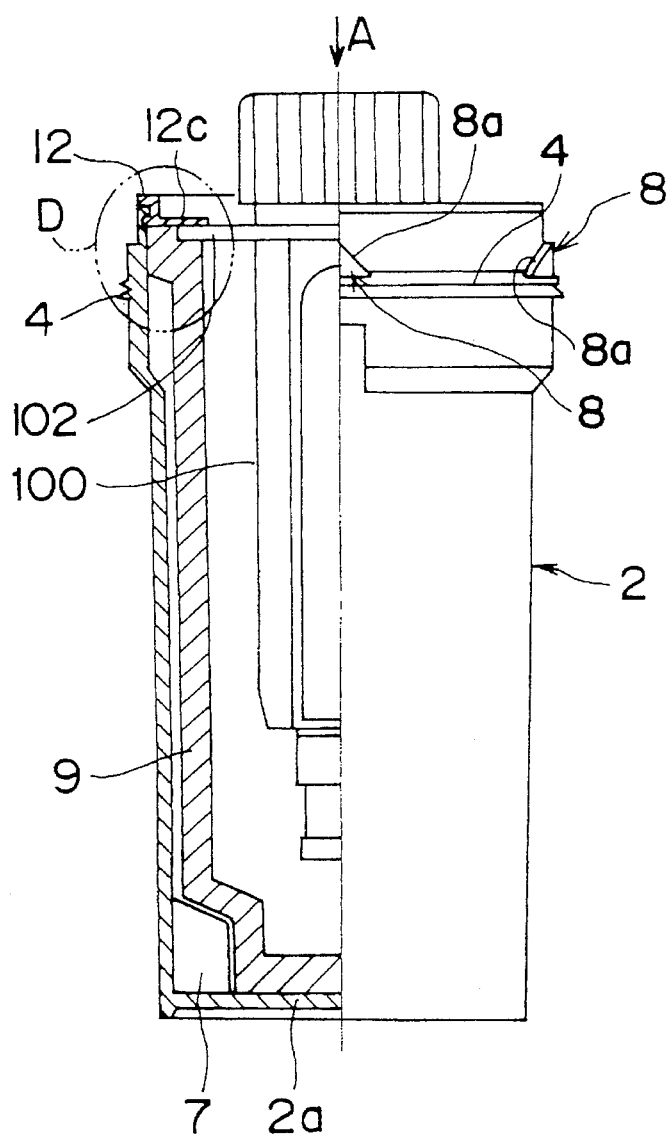
FIG. 2 is a view showing a sheath container and the like constituting the container for transporting the radiation shield member according to the embodiment of the present invention, in which the left side with respect to a center axis is a sectional view of the container, and the right side with respect to the center axis is a front view thereof, with the radiation shield member being inserted in the sheath container.
Figure 7:
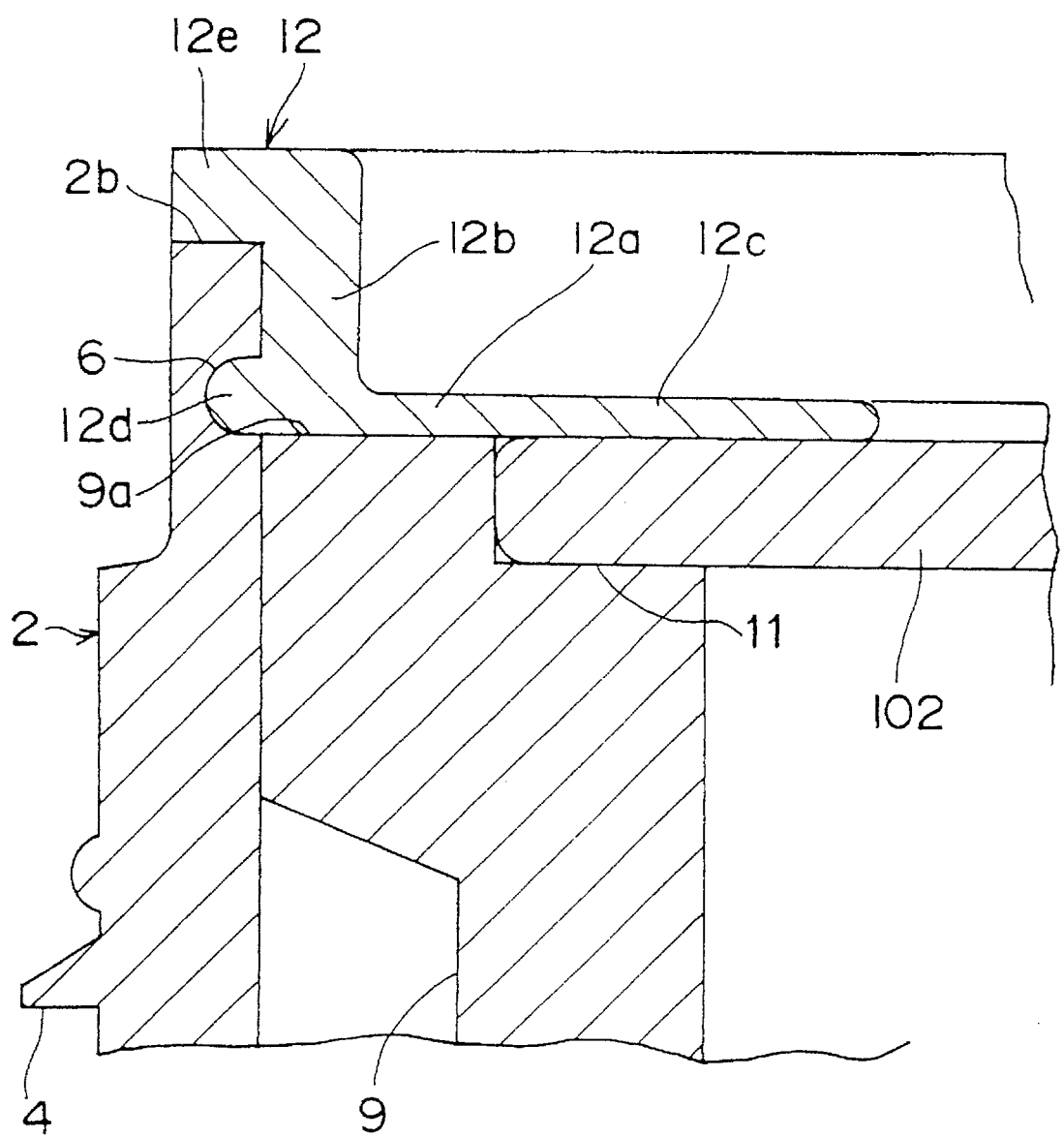
FIG. 7 is an enlarged view of a portion D shown in FIG. 2.

As shown in FIGS. 2 and 7, an annular projection 4 is formed circumferentially on the entire outer peripheral surface of the sheath container 2 in the vicinity of the edge of the opening thereof. An annular groove 5 to engage the annular projection 4 is formed circumferentially on the entire inner peripheral surface of the cover 3 in correspondence to the annular projection 4. The cover 3 keeps the sealing performance of the transport container 1 for transporting the radiation shield member by means of a so-called snap-on method due to the engagement between the annular projection 4 and the annular groove 5 and is removable from the sheath container 2.

Mountain-shaped guide projections 8 as disclosed in Japanese Laid-Open Utility Model Publication No. 55-170262 are formed in the circumferential direction of the sheath container 2 at regular intervals on the peripheral surface thereof in the vicinity of the edge of the opening thereof. In this embodiment, the guide projections 8 are formed at four positions at intervals corresponding to a central angle of 90°. Each guide projection 8 has two inclined slide surfaces 8a.

A groove 6 for installing a holding ring 12 which will be described later is formed circumferentially on the entire inner peripheral surface of the sheath container 2 in the vicinity of the edge of the opening thereof, as shown in FIG. 7.

Further, at a position where a bottom plate 2a of the sheath container 2 is disposed, two plates 7 are erected in parallel with each other at a predetermined interval along the inner peripheral surface of the sheath container 2.

Figure 8:
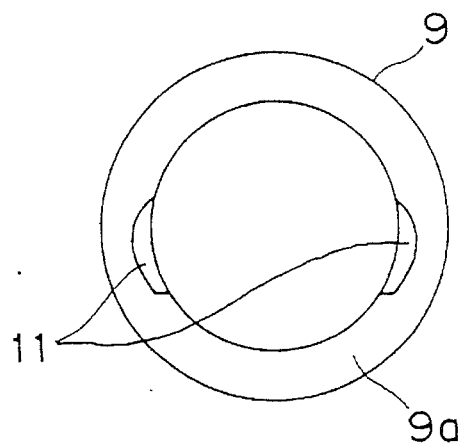
FIG. 8 is a plan view showing a radiation shield container shown in FIG. 2.
Figure 9:
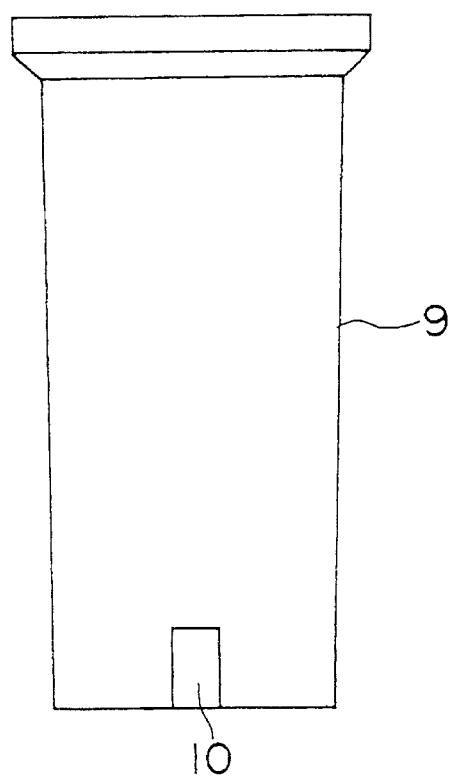
FIG. 9 is a front view showing the radiation shield container shown in FIG. 2.
Figure 10:
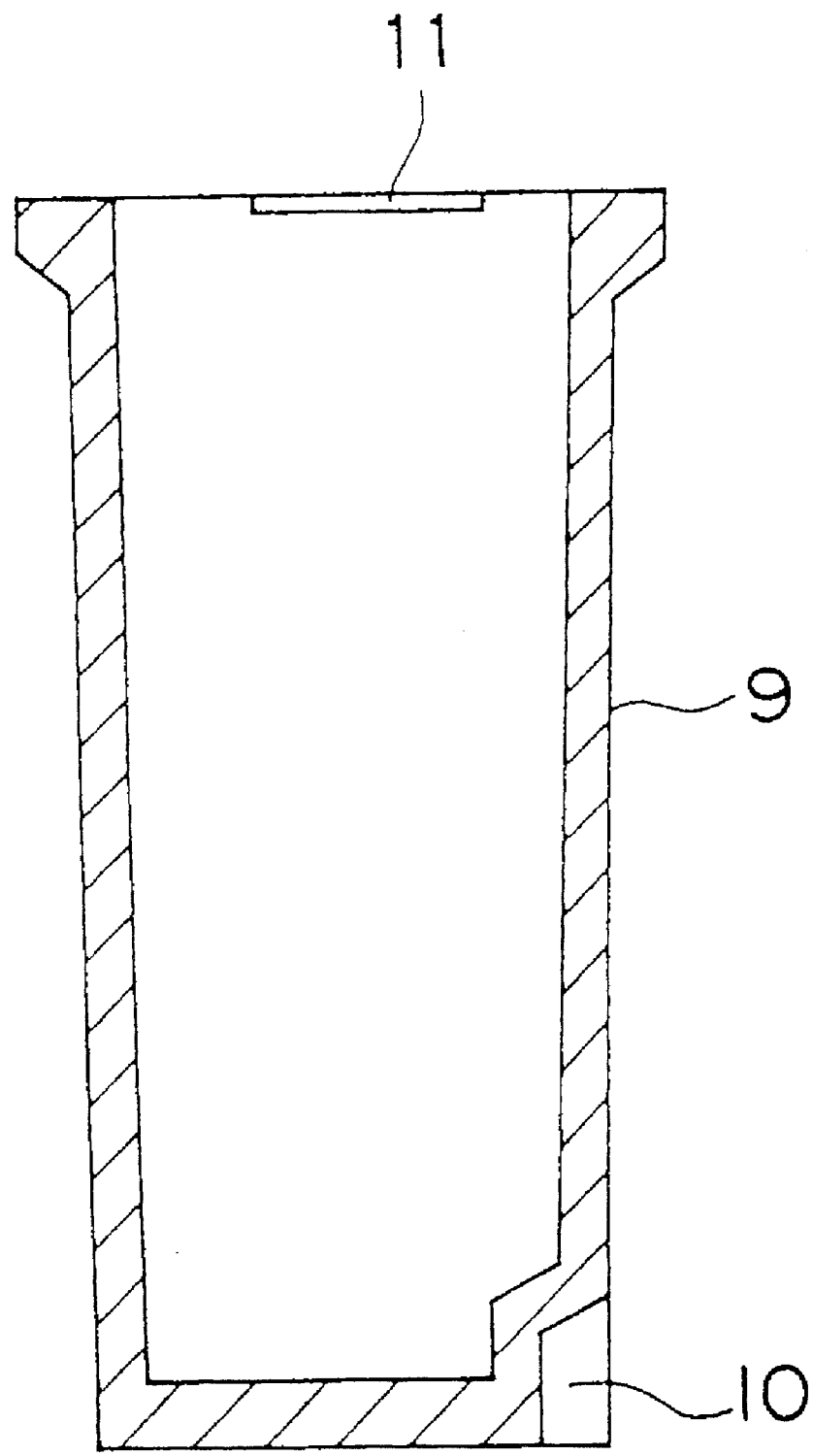
FIG. 10 is a sectional view showing the radiation shield container shown in FIG. 2.

As shown mainly in FIGS. 8 through 10, a cup-shaped radiation shield container 9 is mounted in the sheath container 2. The radiation shield container 9 is made of lead material or the like and shields radiation which has been emitted from the radiopharmaceutical liquid contained in the syringe accommodated in the sheath container 2 and then transmitted through the radiation shield member 100. The outer diameter of the radiation shield container 9 is so set as to generally allow the radiation shield container 9 to contact the inner peripheral surface of the sheath container 2. When the radiation shield container 9 is mounted in the sheath container 2, the end surface 9a of the opening of the radiation shield container 9 is situated at a shorter distance toward the bottom of the sheath container 2 than the end surface 2b of the opening of the sheath container 2 is situated toward the bottom of the sheath container 2, as shown in FIG. 7. As will be described later, the radiation shield container 9 can be prevented from being removed from the sheath container 2 by mounting the holding ring 12 on a stepped portion formed between the end surface 2b and the end surface 9a and mounting the holding ring 12 on the sheath container 2.

When the sheath container 2 is cylindrical as in the case of this embodiment, in order to prevent the radiation shield container 9 from rotating circumferentially in the sheath container 2, a groove 10 having a width a little smaller than the interval between the two plates 7 is formed on the bottom of the radiation shield container 9 so as to press the plates 7 into the groove 10. If the sheath container 2 is not cylindrical, it is unnecessary to form the groove 10.

Concave recesses 11 to be engaged by the wing-shaped holding members 102 which constitutes a part of the radiation shield member 100 when the radiation shield member 100 is accommodated in the radiation shield container 9 are formed on the end surface 9a of the radiation shield container 9. The depth of each concave recess 11 is equal to the thickness of the wing-shaped holding member 102, and the configuration of the concave recess 11 is the same as that of the wing-shaped holding member 102 which contacts the end surface 9a. The radiation shield member 100 is fixed in position in the radiation shield container 9 by the engagement between the concave recess 11 and the wing-shaped holding member 102.

Figure 13:
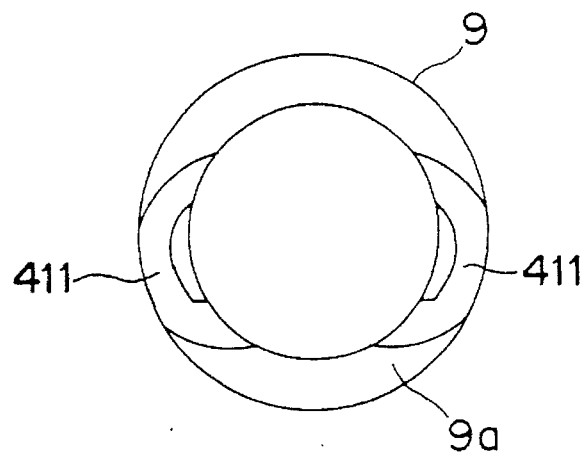
FIGS. 13 and 14 are a plan view and a front view showing the radiation shield container according to a modified embodiment of the present invention.
Figure 14:
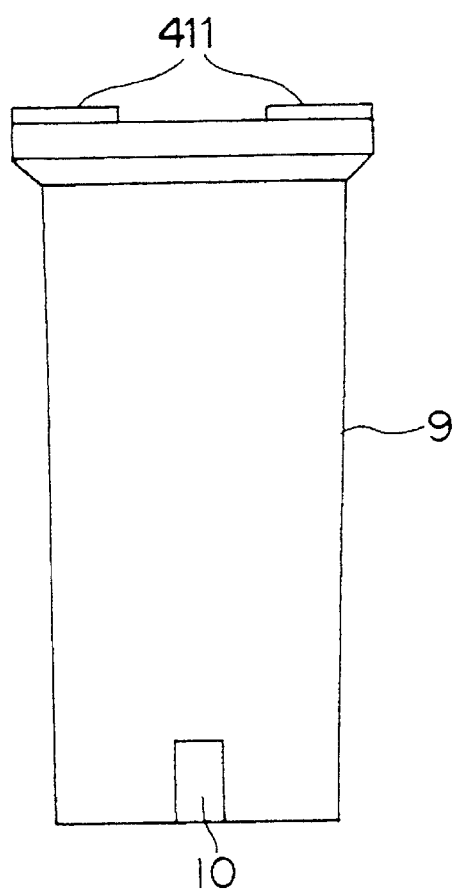
Figure 15:
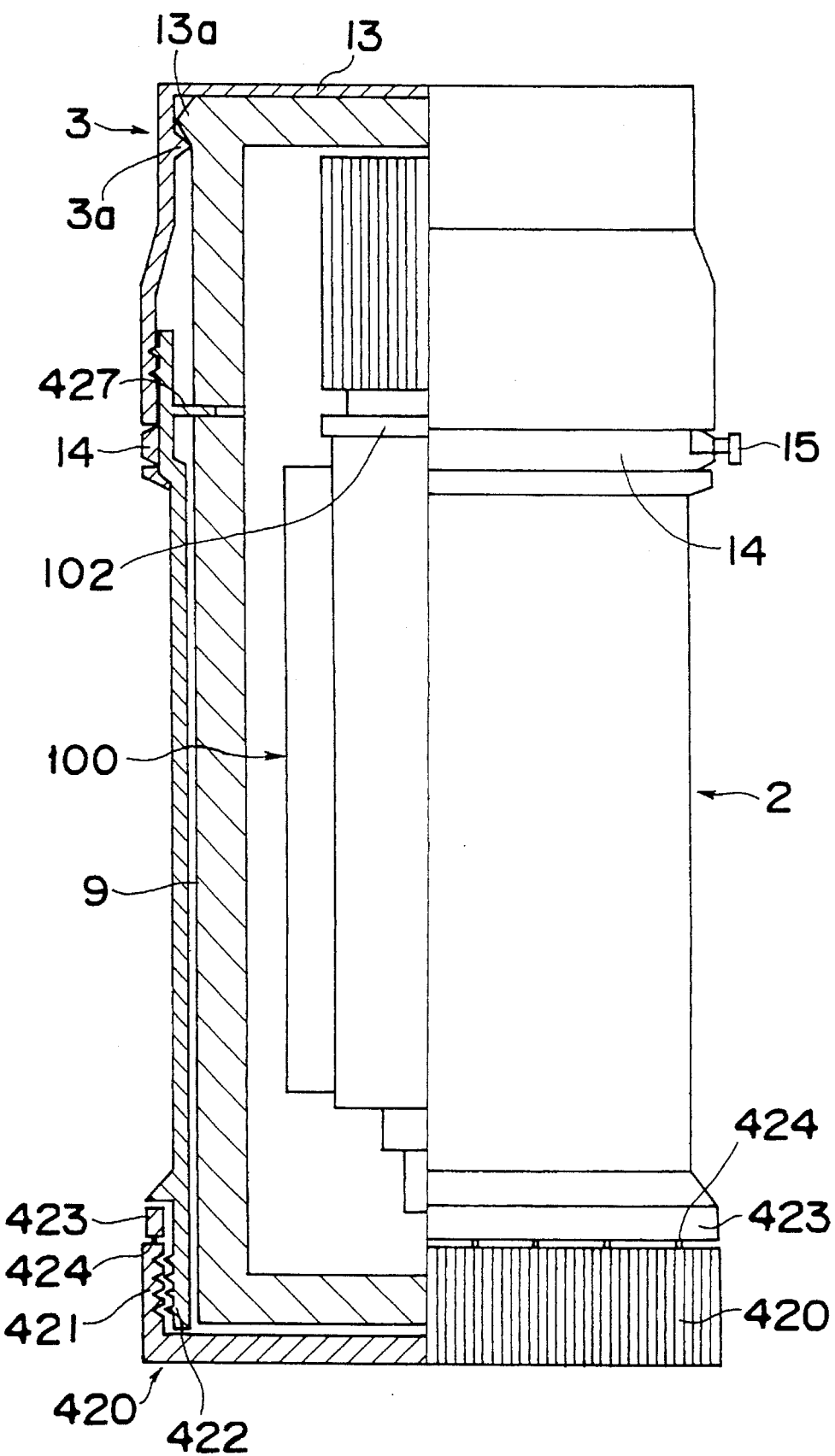
FIG. 15 is a view showing a container for transporting a radiation shield member according to another embodiment of the present invention, in which the left side with respect to a center axis is a sectional view of the transport container, and the right side with respect to the center axis is a front view thereof with the radiation shield member being inserted in the transport container.
Figure 16:
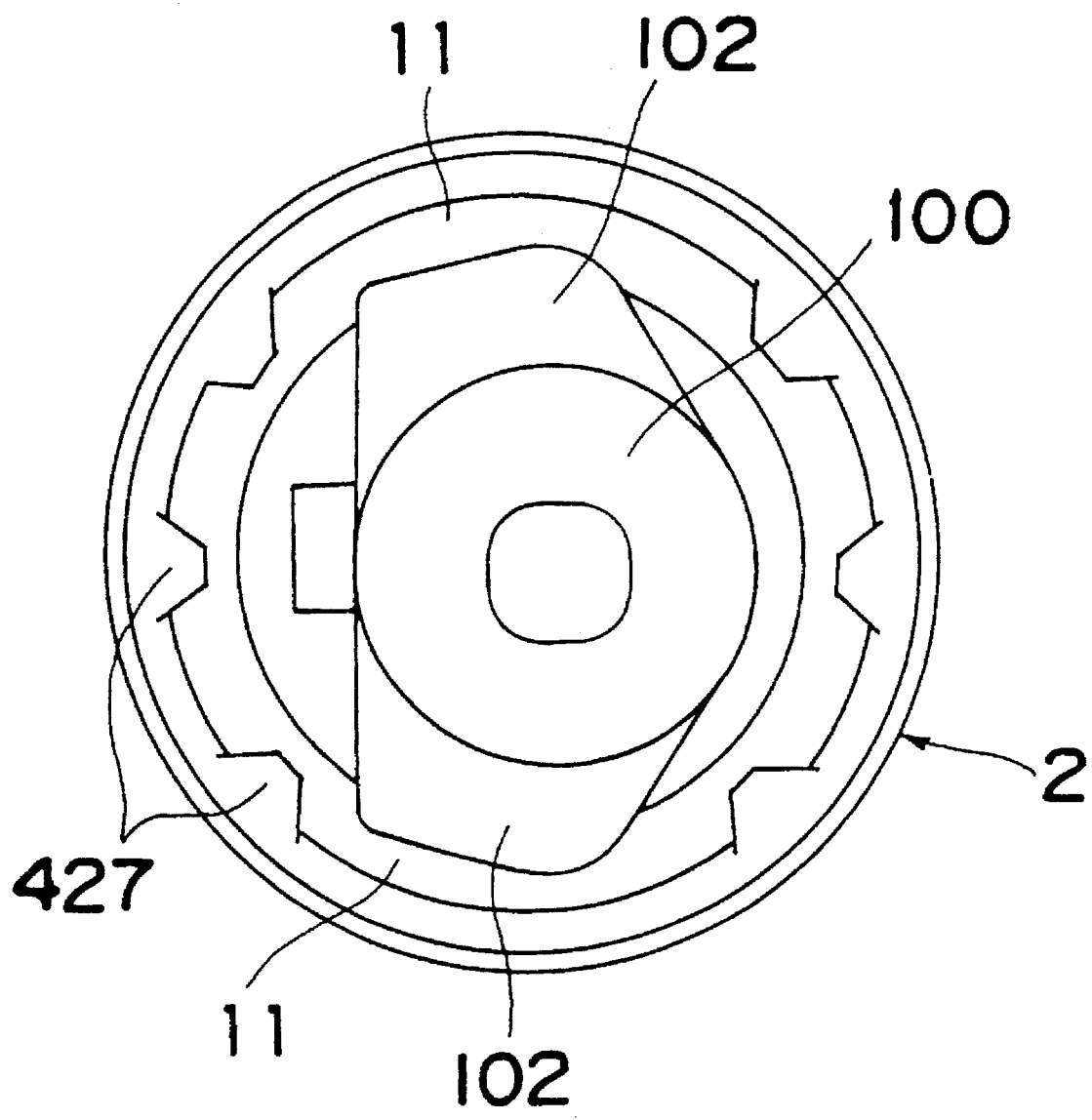
FIG. 16 is a plan view showing the sheath container of the transport container in FIG. 15 with the radiation shield member being inserted in the transport container.
Figure 17:
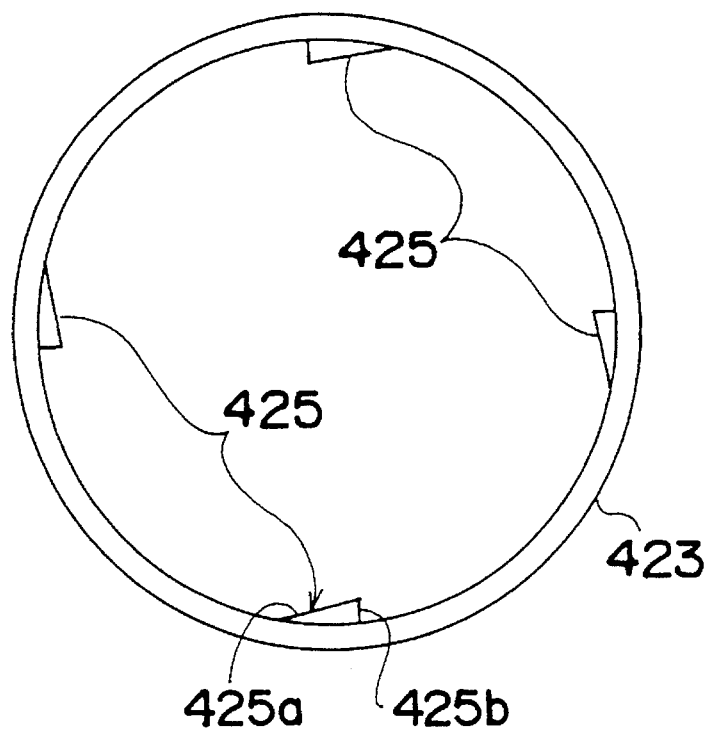
FIG. 17 is a bottom view of a part of a bottom cover mounted onto the bottom of the sheath container in FIG. 15.
Figure 18:
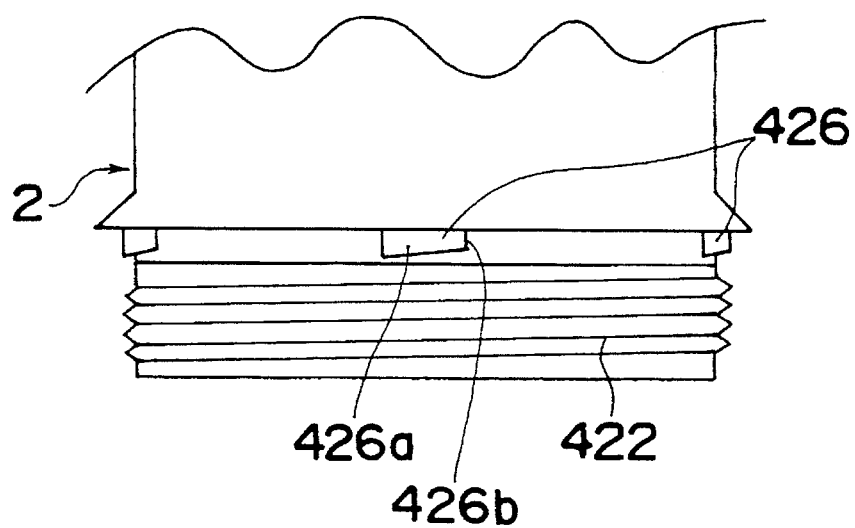
FIG. 18 is a partial side view of the outer side surface in the vicinity of the sheath container in FIG. 15.

Although the concave recess 11 is adopted in this embodiment as a position-fixing portion for fixing the wing-shaped holding member 102 in position, the position-fixing portion for fixing the wing-shaped holding member 102 in position is not limited to a portion having a concave configuration. For example, as shown in FIGS. 13 and 14, a portion may be constituted by projections 411 erected on the end surface 9a and capable of contacting the other peripheral surface of the wing-shaped holding members 102.

Figure 5:
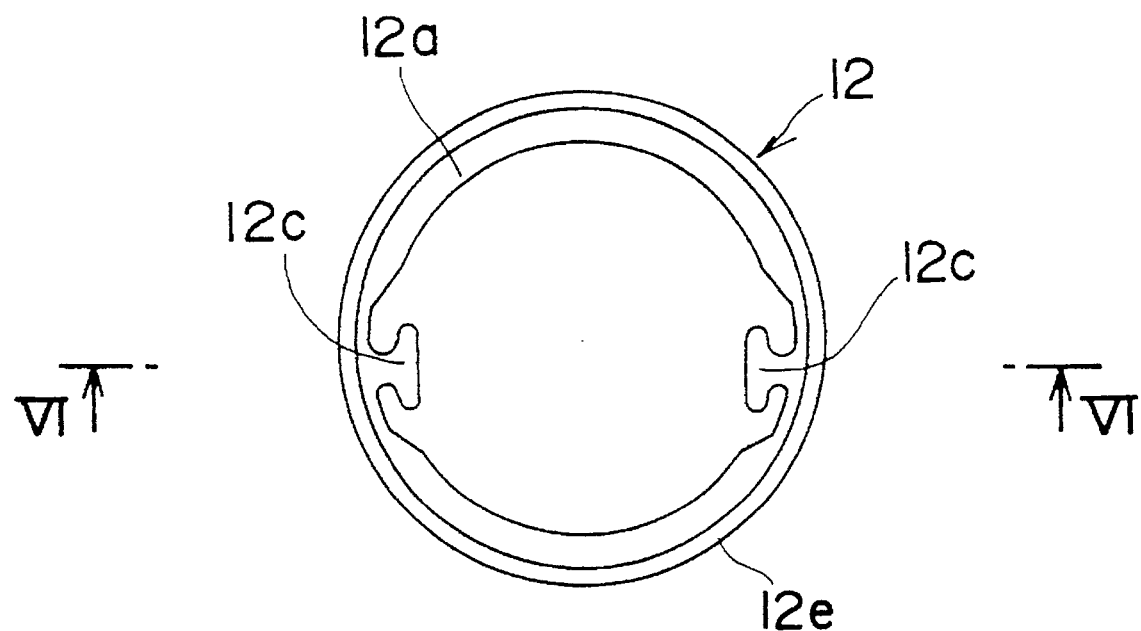
FIG. 5 is a plan view showing a holding ring shown in FIG. 2.
Figure 6:
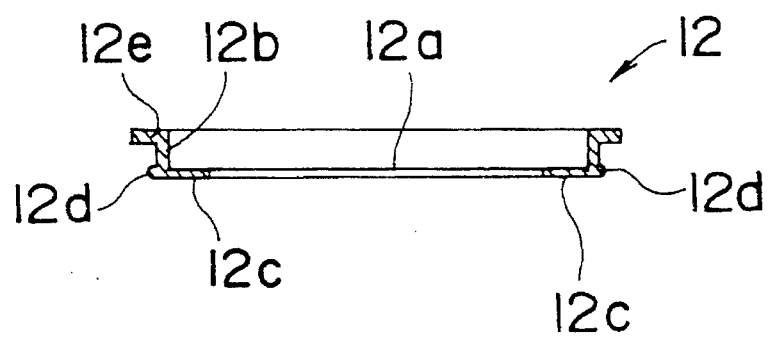
FIG. 6 is a sectional view, of the holding ring, taken along a line VI—VI of FIG. 5.

As shown in mainly FIGS. 5 through 7, the holding ring 12 is an annular member approximately U-shaped in section and having a through-hole in the center thereof. As shown in FIG. 7, the holding ring 12 comprises a cylindrical portion 12b engaging the inner peripheral surface of the sheath container 2; an approximately ring-shaped shield container removal-preventing portion 12a extending from the cylindrical portion 12b toward the center of the holding ring 12; and an approximately T-shaped shield member removal-preventing portion 12c extending from two positions, opposed to each other, of the shield container removal-preventing portion 12a toward the center of the holding ring 12. An annular projection portion 12d which engages the holding ring-installing groove 6 formed on the inner peripheral surface of the sheath container 2 is circumferentially formed on the entire outer peripheral surface, of the cylindrical portion 12b, which contacts the inner peripheral surface of the sheath container 2. Considering a possible removal of the holding ring 12 from the sheath container 2, preferably, the projection portion 12d is semicircular in section as shown in the drawings.

The holding ring 12 is mounted on the opening of the sheath container 2 by engaging the cylindrical portion 12b with the inner peripheral surface of the sheath container 2 and by engaging the projection portion 12d with the holding ring-installing groove 6. A projection portion 12e projecting radially and outwardly from the cylindrical portion 12b contacts the end surface 2b of the sheath container 2.

Figure 4:
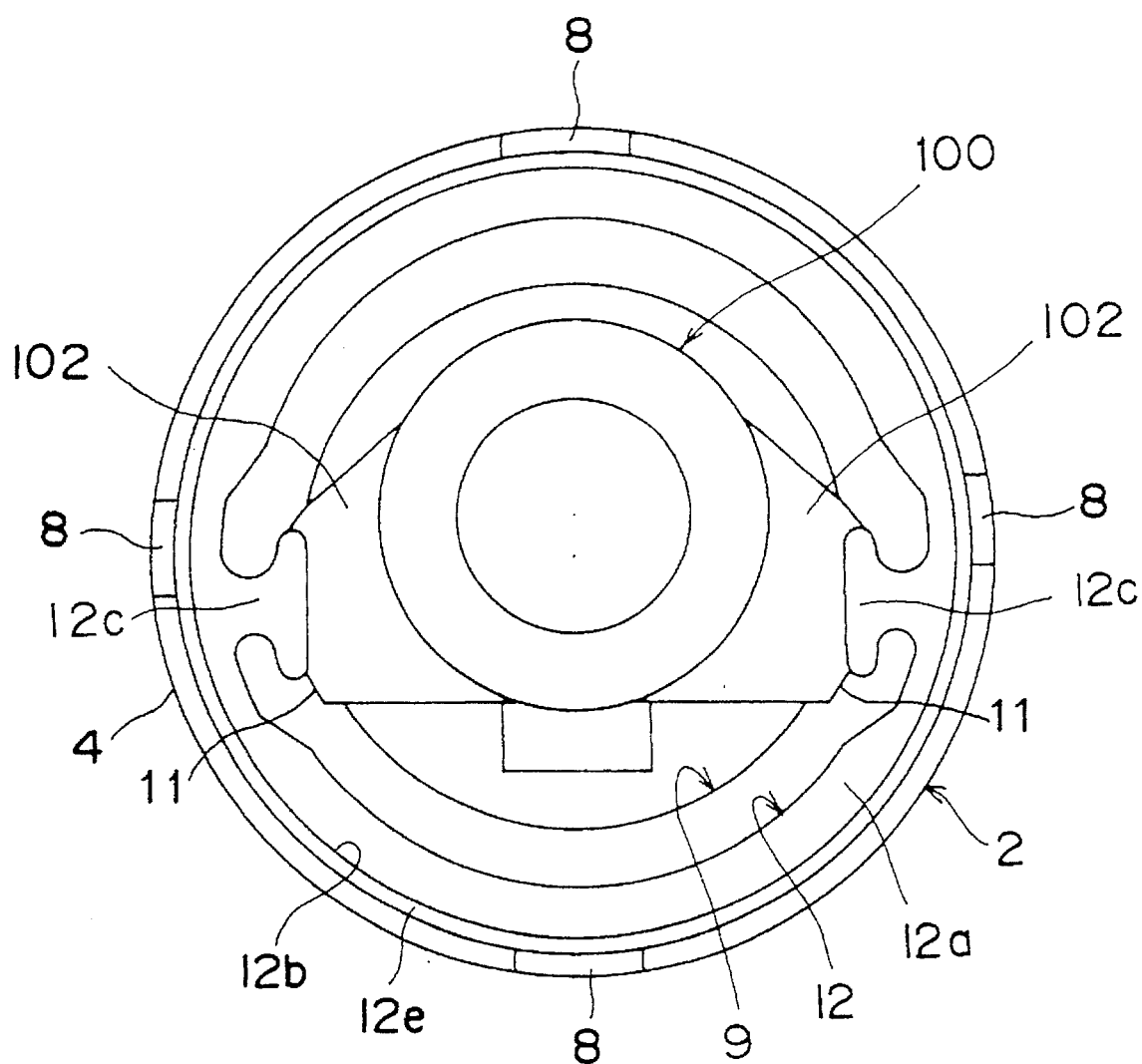
FIG. 4 is a plan view obtained by viewing the sheath container of the container for transporting the radiation shield member shown in the direction of arrow A of FIG. 2 with the radiation shield member being inserted in the sheath container.

As a result of the mounting of the holding ring 12 on the sheath container 2, the shield container removal-preventing portion 12a is brought into contact with the end surface 9a of the opening of the radiation shield container 9, thus preventing the radiation shield container 9 from being removed from the sheath container 2 and in addition, the shield member removal-preventing portion 12c prevents the radiation shield member 100 from being removed from the radiation shield container 9, because the shield member removal-preventing portion 12c extends in such a direction and a configuration as to cover and contact the wing-shaped holding members 102 engaged by the concave recesses 11 of the radiation shield container 9, as shown in FIG. 4. Although in the illustration, the thickness of the shield container removal-preventing portion 12a is equal to that of the shield member removal-preventing portion 12c, actually, for example, the thickness of the shield container removal-preventing portion 12a is 0.5 mm and that of the shield member removal-preventing portion 12c is 0.3 mm. That is, the thickness of the shield member removal-preventing portion 12c is very small.

Figure 11:
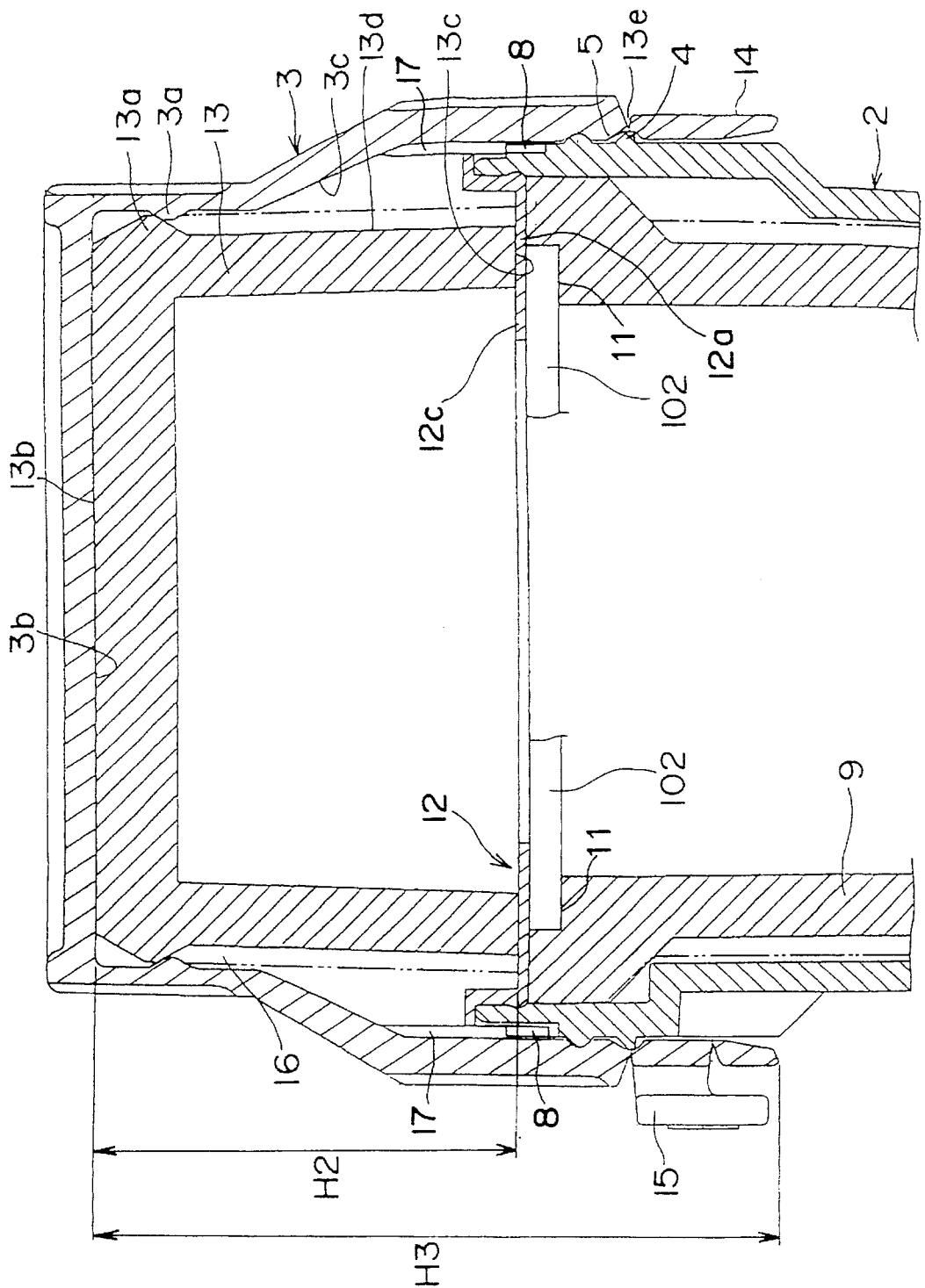
FIG. 11 is a sectional view showing a state in which the cover shown in FIG. 1 is mounted on the sheath container shown in FIG. 2 with the radiation shield member being inserted in the sheath container.

As shown in FIGS. 1 and 11, the cover 3 is cup-shaped and mounted on the edge of the opening of the sheath container 2, thus closing the opening of the sheath container 2. A projection 3a approximately half-elliptic in section is formed circumferentially on the entire inner peripheral surface of the cover 3 in the vicinity of the upper end of the cover 3. A cup-shaped radiation shield member 13 made of lead material and having a projection 13a, engaging the projection 3a, formed on the outer peripheral surface thereof is held inside the cover 3. That is, with the upper surface 13b of the top portion of the cup-shaped lead radiation shield member 13 in contact with the inner surface 3b of the top portion of the cover 3, the projection 3a of the cover 3 engages the projection 13a of the cup-shaped lead radiation shield member 13, thus holding the cup-shaped lead radiation shield member 13 inside the cover 3.

In order to separate the cup-shaped lead radiation shield member 13 from the cover 3 more easily, a gap 16 having an appropriate amount of space is formed between the outer peripheral surface 13d of the cup-shaped lead radiation shield member 13 and the inner peripheral surface 3c of the cover 3. The gap 16 performs a function of allowing the cover 3 to be flexible, thus facilitating the opening and closing of the cover 3. In order to separate the cover 3 from the cup-shaped lead radiation shield member 13, for example, a thumb of one hand is inserted into the inside of the cup-shaped lead radiation shield member 13 and a forefinger of the hand contacts the outer side surface of the cover 3 to pick them to reduce the gap between the cup-shaped lead radiation shield member 13 and the cover 3, thus easily taking out the cup-shaped lead radiation shield member 13 from the cover 3.

Inverted mountain-shaped cover side-guide projections 17 having two inclined slide surfaces 17a is formed on the inner peripheral surface 3c disposed in the vicinity of the opening edge of the cover 3, in correspondence with the guide projections 8 formed on the outer peripheral surface of the sheath container 2. By rotating the cover 3 in the circumferential direction thereof, one of the slide surfaces 8a of each guide projection 8 and one of the slide surfaces of each cover side-guide projection 17 slide in contact with each other, thus outwardly moving the cover 3 in the axial direction of the sheath container 2 and separating the cover 3 from the sheath container 2.

The height H2 of the cup-shaped lead radiation shield member 13 is so set that when the annular groove 5 formed on the cover 3 and the annular projection 4 formed on the sheath container 2 are in engagement with each other, the lower end surface 13c of the cup-shaped lead radiation shield member 13 contacts the shield container removal-preventing portion 12a of the holding ring 12 as well as the shield member removal-preventing portion 12c thereof. Thus, the wing-shaped holding members 102 of the radiation shield member 100 are held firmly by means of the cup-shaped lead radiation shield member 13 and the radiation shield container 9 via the shield container removal-preventing portion 12a and the shield member removal-preventing portion 12c, with a force being applied to the wing-shaped holding members 102 of the radiation shield member 100 in the axial direction thereof.

In the cover 3, an annular notch 13e is formed circumferentially on the entire outer peripheral surface of the cover 3 in correspondence to the annular groove 5, and the thickness of a portion, of the cover 3, sandwiched between the annular groove 5 and the annular notch 13e is much smaller than the thicknesses of other portions of the cover 3. The opening side of the cover 3 disposed below the annular notch 13e is denoted as the sealing connection portion 14. The art of the sealing connection portion proposed by the present applicant and disclosed in Japanese Utility Model Publication No. 5-24078 is adopted in forming the sealing connection portion 14. That is, the knob 15 is pulled to the cover 3 and rotated around the cover 3, and then the sealing connection portion 14 is separated from the cover 3 at the annular notch 13e to break the seal between the cover 3 and the sheath container 2 to take out the cover 3 from the sheath container 2.

The sealing connection portion 14 prevents danger that the cover 3 is loosened from the sheath container 2 or the cover 3 is opened or closed by accident during transport. The sealing connection portion 14 is separated from the cover 3 at the annular notch 13e, and hence the cover 3 can be removed from the sheath container 2 by pulling a knob 15 formed on the sealing connection portion 14. In addition, the break of the sealing connection portion 14 from the cover 3 indicates that the radiopharmaceutical liquid has been used.

In the transport container 1 for transporting the radiation shield member, according to this embodiment, having the above-described construction, the radiation shield member 100 containing the syringe is accommodated in the transport container 1 by engaging each wing-shaped holding member 102 with each concave recess 11 formed on the end surface 9a of the radiation shield container 9 and by preventing the movement of the radiation shield member 100 in the axial direction of the transport container 1 by means of the holding ring 12. Further, as a result of the mounting of the cover 3 on the sheath container 2 so as to close the opening of the sheath container 2 by the cover 3, the end surface 13c of the cup-shaped lead radiation shield member 13 inside the cover 3 is brought into contact with the holding ring 12, and then the opening of the sheath container 2 is sealed by the cover 3. In this state, the radiation shield member 100 is held firmly in the transport container 1. That is, in the state in which the opening of the sheath container 2 is sealed by the cover 3, the radiation shield member 100 is prevented from moving in the axial direction of the transport container 1 and further, the leading end of the radiation shield member 100 is prevented from pivoting on the wing-shaped holding members 102 in the radiation shield container 9.

In taking out the radiation shield member 100 from the transport container 1, the knob 15 of the sealing connection portion 14 is pulled to break and remove the sealing connection portion 14 from the cover 3 by cutting the sealing connection portion 14 at the annular notch 13e. In this manner, the transport container 1 sealed by the cover 3 which has closed the sheath container 2 is unsealed.

By rotating the cover 3 in the circumferential direction thereof, the slide surfaces 8a of the guide projections 8 of the sheath container 2 and the slide surfaces 17a of the cover side-guide projections 17 of the cover 3 slide in contact with each other, thus moving the cover 3 in the axial direction of the sheath container 2 and separating the sheath container 2 from the cover 3. As a result of the removal of the cover 3 from the sheath container 2, the head of the radiation shield member 100 is exposed to the outside. By pulling the head in the axial direction of the transport container 1, the wing-shaped holding members 102 press the shield member removal-preventing portion 12c of the holding ring 12 upward. In this manner, the radiation shield member 100 is removed from the transport container 1.

As described above, in the container for transporting the radiation shield member according to this embodiment, the radiation shield member 100 can be held in the transport container 1 reliably and stably by providing a radiation shield container 9 having an inner diameter shorter than the length of the total of the two wing-shaped holding members 102 of the radiation shield member 100 and by providing on the radiation shield container 9 the concave recesses 11, having the same configurations in plan view as those of the wing-shaped holding members 102, to be engaged by the wing-shaped holding members 102. Thus, it is unnecessary to provide a cushioning material for supporting the radiation shield member 100 in the transport container 1, and the outer diameter of the radiation shield container 9 can be reduced and thus a compact and light transport container 1 can be provided. Further, since each concave recess 11 has the same plan configuration as that of each wing-shaped holding member 102, the radiation shield member 100 can be taken out from the radiation shield container 9 easily.

Since the cup-shaped lead radiation shield member 13 is mounted in the cover 3 by engaging the projection 3a of the cover 3 with the projection 13a of the cup-shaped lead radiation shield member 13, the cup-shaped lead radiation shield member 13 can be easily mounted on the cover 3 in the manufacturing operation, and the cup-shaped lead radiation shield member 13 mounted in the cover 3 can be removed from the sheath container 2 together with the cover 3 by removing the cover 3 from the sheath container 2. In order to separate the cover 3 from the cup-shaped lead radiation shield member 13, for example, a thumb of one hand is inserted into the inside of the cup-shaped lead radiation shield member 13 and a forefinger of the hand contacts the outer side surface of the cover 3 to pick them to reduce a gap between the cup-shaped lead radiation shield member 13 and the cover 3, thus easily taking out the cup-shaped lead radiation shield member 13 from the cover 3. Accordingly, the cup-shaped lead radiation shield member 13 can be reused. Moreover, since the gap 16 is formed between the inner peripheral surface 3c of the cover 3 and the outer peripheral surface 13d of the cup-shaped lead radiation shield member 13, the cover 3 is allowed to be flexible and thus can be easily installed on the sheath container 2 or removed therefrom. As apparent from the above description, the present invention can provide the transport container which has a favorable operability and allows a reusable material and a non-reusable material to be easily separated from each other for classified refuse.

Furthermore, since the shield member removal-preventing portion 12c is formed on the holding ring 12, and a part of each wing-shaped holding member 102 of the radiation shield member 100 is covered with the shield member removal-preventing portion 12c, the radiation shield member 100 accommodated in the sheath container 2 can be prevented from popping out therefrom even though the sheath container 2 upsets in the state in which the cover 3 has been removed from the sheath container 2. Since the shield member removal-preventing portion 12c is constituted by a thin plate, the shield member removal-preventing portion 12c is bent by pulling the head of the radiation shield member 100 in the axial direction of the transport container 1 and consequently, the radiation shield member 100 can be taken out from the transport container 1.

In addition, since the holding ring 12 is mounted on the sheath container 2 by the engagement between the projection portion 12d and the holding ring-installing groove 6 of the sheath container 2, the holding ring 12 can be removed from the sheath container 2, and the radiation shield container 9 can be separated from the sheath container 2 for the disposal of the sheath container 2 by removing the holding ring 12 from the sheath container 2 and pulling the radiation shield container 9 in the axial direction of the transport container 1. Thus, the radiation shield container 9 can be reused.

Further, the sheath container 2 and the radiation shield container 9 are provided with the plates 7 and the groove 10 engaging the plates 7, respectively so as to prevent the radiation shield container 9 from rotating relative to the sheath container 2. Thus, the position relationship between the shield member removal-preventing portion 12c and the wing-shaped holding members 102 is maintained. That is, the state in which the shield member removal-preventing portion 12c covers a part of the wing-shaped holding members 102 is prevented from being altered.

FIGS. 15–18 show a transport container for transporting a radiation shield member according to another embodiment of the present invention. In this embodiment, there is no holding ring 12 and instead, a plurality of approximately trapezoidal engaging projections 427 are integrally formed to project inwardly from the inner peripheral surface of the opening end of the sheath container 2 to contact the engaging projections 427 with the end surface of the opening end of the radiation shield container 9 to prevent the radiation shield container 9 from being removed from the sheath container 2. The two wing-shaped holding members 102 of the radiation shield member 100 are engaged in the concave recesses 11 serving as the position-fixing portion and provided at the end surface 9a of the radiation shield container 9 in the sheath container 2 to fix the radiation shield member 100 between the cover 3 and the cup-shaped lead radiation shield member 13. The depth of the concave recess 11 is smaller than the thickness of the wing-shaped holding member 102, and thus the wing-shaped holding members 102 engaged in the concave recesses 11 are held between the cup-shaped lead radiation shield member 13 of the cover 3 and the radiation shield container 9 of the sheath container 2 to reliably fix the radiation shield member 100 in the transport container. On the other hand, as a result of the provision of the engaging projections 427, in order to prevent it from being difficult that the radiation shield container 9 is taken out from the sheath container 2, an opening is formed at the bottom of the sheath container 2 and a bottom cover 420 is provided to cover the opening. Then, the bottom cover 420 is taken out from the sheath container 2 to easily take out the radiation shield container 9 through the opening of the bottom of the sheath container 2. The bottom cover 420 is made of elastic synthetic resin and has a female screw 421 at its body portion for engaging a male screw 422 formed at the outer side surface in the vicinity of the bottom opening of the sheath container 2. The bottom cover 420 also has a ring portion 423 connected to the body portion of the bottom cover 420 via a plurality of connecting portions 424 for easily cutting out from the body portion. The ring portion 423 has four wedges 425 at its inside to engage the four wedges 425 with wedges 426 of the male screw 422 of the sheath container 2. That is, when the female screw 421 of the bottom cover 420 is engaged with the male screw 422 of the sheath container 2 to mount the bottom cover 420 onto the sheath container 2, an inclined slide surface 425a of each wedge 425 of the bottom cover 420 is slid on an inclined slide surface 426a of each wedge 426 of the sheath container 2. When the bottom cover 420 is rotated and taken out from the sheath container 2, an engaging surface 425b of each wedge 425 of the bottom cover 420 contacts an engaging surface 426b of each wedge 426 of the sheath container 2 to prevent rotation. Then, when the bottom cover 420 is further rotated to the sheath container 2, the connecting portions 424 between the ring portion 423 and the body portion of the bottom cover 420 are cut to leave the ring portion 423 on the side of the sheath container 2 and take out the bottom cover 420 from the sheath container 2. A sealing connection mechanism similar to the sealing connection mechanism between the cover 3 and the sheath container 2 is formed between the bottom cover 420 and the sheath container 2. The engaging projections 427 are not limited to be integrally fixed to the sheath container 2 but may be removably fixed thereto.

According to this embodiment shown in FIGS. 15–18, the two wing-shaped holding members 102 of the radiation shield member 100 are fixedly held between the cup-shaped lead radiation shield member 13 of the cover 3 and the radiation shield container 9 of the sheath container 2, and thus it is unnecessary to provide a cushioning material in conformity with the outer diameter of the radiation shield member 100 which is provided in the conventional transport container and the outer diameter the entire transport container can be reduced and the transport container can be light in weight and have favorable operability.

Figure 19:
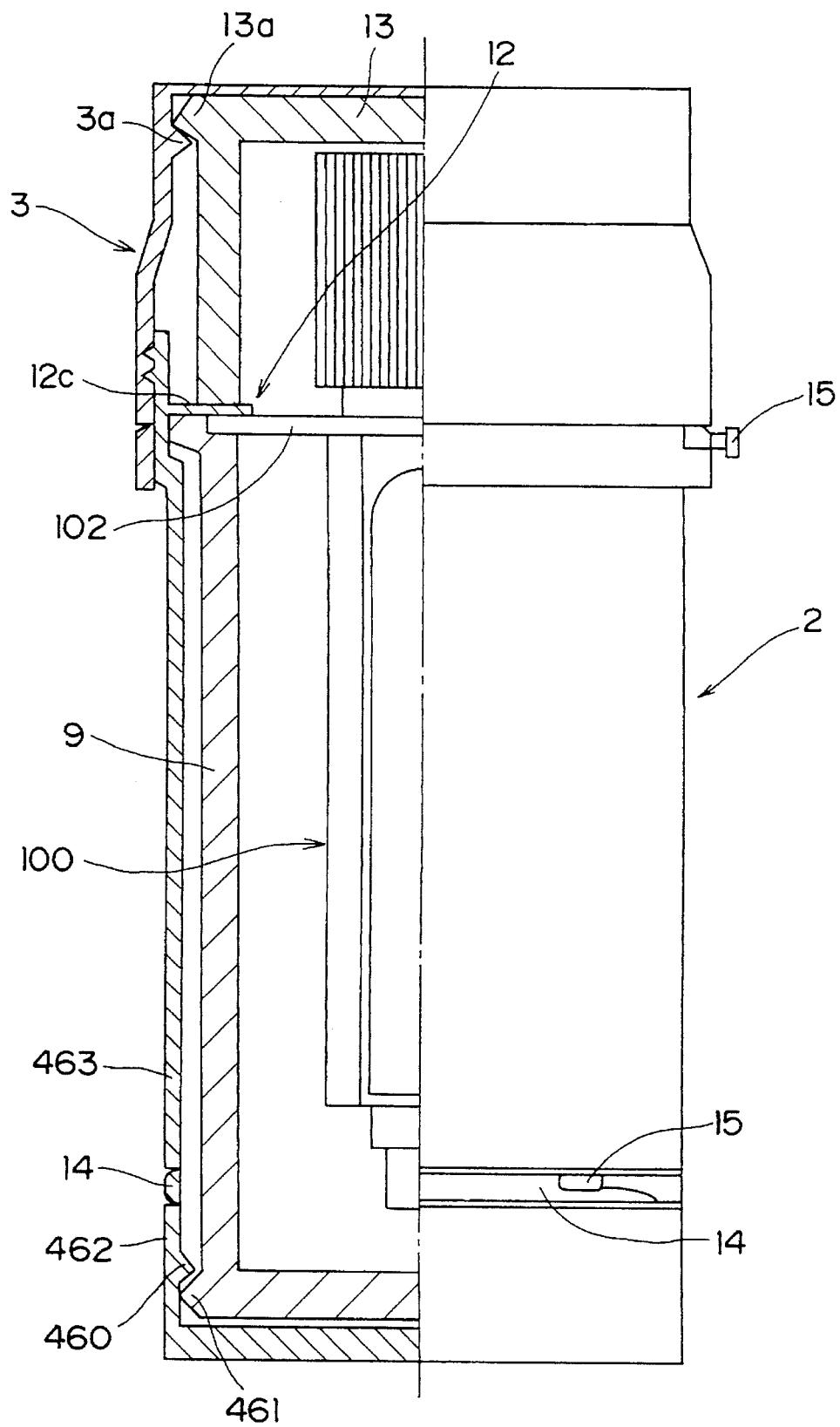
FIG. 19 is a view showing a container for transporting a radiation shield member according to a further embodiment of the present invention, in which the left side with respect to a center axis is a sectional view of the transport container, and the right side with respect to the center axis is a front view thereof with the radiation shield member being inserted in the transport container.

FIG. 19 shows a transport container for transporting a radiation shield member according to a further embodiment of the present invention with the radiation shield member 100 being inserted therein.

In this embodiment, there is provided the holding ring 12 but the holding ring 12 has only the shield member removal-preventing portion 12c and does not have the shield container removal-preventing portion 12a. A mechanism for preventing the shield container 9 from being removed from the sheath container 2 is provided on the side of the bottom of the sheath container 2. That is, an annular projection 460 is provided at the inner surface of the bottom of the sheath container 2 and the projection 460 is engaged with an annular projection 461 formed on the outer surface of the bottom of the shield container 9 to engage the shield container 9 with the sheath container 2 for preventing removal thereof. In order to release the engagement between the projections 460 and 461 of the shield container 9 and the sheath container 2, a mechanism similar to the sealing connection mechanism between the cover 3 and the sheath container 2 is provided. That is, the knob 15 and the sealing connection portion 14 etc. are provided at a portion in the vicinity of the bottom of the sheath container 2. The sealing connection is broken by the knob 15 to separate the bottom-side portion 462 of the sheath container 2 from the body portion-side portion 463 thereof, and thus the engagement between the two projections 460 and 461 is released. After releasing the engagement between the two projections, when the holding ring 12 is removed from the sheath container, the shield container 9 can be easily taken out from the sheath container 2. In this embodiment, such a mechanism that the two wing-shaped holding members 102 of the radiation shield member 100 are fixedly held between the cup-shaped lead radiation shield member 13 of the cover 3 and the shield container 9 of the sheath container 2 can be adopted. The shield member removal-preventing portion 12c is not limited to be provided at the holding ring 12 but may be integrally fixed to the sheath container 2 or may be removably fixed thereto. When the shield member removal-preventing portion 12c is integrally fixed to the sheath container 2, the portion 12c is broken or the sheath container 2 itself is broken to take out the shield container 9 for disposal.

Although the mountain-shaped and inverted mountain-shaped guide projections 8, 17 are formed on each of the sheath container 2 and the cover 3 in the above-described embodiment, the cover 3 and the sheath container 2 may be fixed to each other with screws. Further, each of the cup-shaped sheath container 2, the radiation shield container 9, and the cover 3 according to the above-described embodiment is not limited to a cylindrical member having a bottom, i.e. a member having a ring-shaped section and having a bottom, but may be a member having a rectangular, square, or polygon frame-shaped section and having a bottom. If the sheath container 2, the radiation shield container 9, and the cover 3 are rectangular, square, or polygon, preferably, the holding ring 12 has a configuration in conformity with the configuration thereof.

In addition to plastic having a high degree of hardness, metal such as stainless steel, aluminum, tungsten or the like may be preferably used as the material of the wing-shaped holding member 102 of the radiation shield member 100.

Preferably, a sheet made of liquid absorbing polymer such as ethylene-acrylate copolymer is provided in a space between the radiation shield container 9 and the radiation shield member 100.

Instead of lead, heavy metal such as tungsten having radiation-shielding capability may be used as the material of the radiation shield container 9 and that of the cup-shaped lead radiation shield member 13 of the cover 3.

The means for fixing the cup-shaped lead radiation shield member 13 to the cover 3 and the means for fixing the radiation shield container 9 to the sheath container 2 are not limited to the construction of the embodiments described but may use an adhesive double coated tape or an adhesive. In this modification, a gap between the members to be fixed to each other is preferably formed so as to easily separate them from each other for disposal.

When ABS resin, polyethylene, polystyrene, vinyl chloride resin, or elastic material, most preferably ABS resin, is used for the material of the cover 3 and the sheath container 2, the cup-shaped lead radiation shield member 13 and the radiation shield container 9 can easily be taken out from the cover 3 and the sheath container 2, respectably, and the cover 3 and the sheath container 2 can easily be cut and torn. When the sheath container has a thin notch, it is easy to tear the sheath container 2 at the thin notch and separate the radiation shield container 9 from the sheath container 2, irrelevant to the fixing with an adhesive.

Furthermore, compared with the conventional transport container, the container for transporting a radiation shield member according to the embodiment of the present invention can have the longer cover 3 and an appropriate weight, can be easy to grip, can be so devised as to allow the cover 3 to be flexible, and in addition, so devised based on human engineering as to easily remove the cover 3 from the sheath container 2.

As described above, according to the container for transporting a radiation shield member of the present invention, the position-fixing portion (for example, concave recesses 11, projections 411, end surface 9a) for fixing the wing-shaped holding members of the radiation shield member including the syringe is formed on the radiation shield container to hold the wing-shaped holding members thereof, and thus the wing-shaped holding members can be reliably fixed in the radiation shield container and the diameter of the radiation shield container can be reduced.

When the container for transporting a radiation shield member of the present invention includes the holding frame (for example, holding ring 12), the shield member removal-preventing portion (for example, 12c) can be formed on the holding frame to prevent the radiation shield member from being removed from the radiation shield container. Thus, the radiation shield container and the holding frame can be light in weight and can prevent the radiation shield member accommodating the syringe in which radiopharmaceutical liquid has been filled from popping out therefrom by accident. The radiation shield container and the sheath container can be easily separated from each other by providing the holding frame for disposal.

Furthermore, when the transport container includes the fifth engaging portion (for example, projection 3a) and the sixth engaging portion (for example, projection 13a), the fifth and sixth engaging portions allow the radiation shield member to be mounted in the cover, and thus the cover is taken out from the sheath container and at the same time the radiation shield member provided at the cover is also taken out from the sheath container to provide a transport container having favorable operability and easily separate the radiation shield member from the cover for disposal.

Moreover, when the position-fixing portion for fixing the wing-shaped holding members of the radiation shield member including the syringe is provided on the radiation shield container and the shield member removal-preventing portion for preventing the radiation shield member from being removed from the radiation shield container is provided on the holding frame, the radiation shield member can be prevented from being rotated and moved in its axial direction in the radiation shield container. This construction eliminates the other constituent members for fixing the radiation shield member to the interior of the radiation shield container. Thus, the transport container can be light in weight and can prevent the radiation shield member accommodating the syringe in which radiopharmaceutical liquid has been filled from popping out therefrom by accident.

Although the present invention has been fully described in connection with the preferred embodiments thereof with reference to the accompanying drawings, it is to be noted that various changes and modification are apparent to those skilled in the art. Such changes and modifications are to be understood as included within the scope of the present invention as defined by the appended claims unless they depart therefrom.

What is claimed is:

1. A transport container for accommodating a radiation shield member to which a syringe having radiopharmaceutical liquid filled thereinto is mounted, the radiation shield member having a wing-shaped holding member at an opening end thereof, the transport container comprising:

a cup-shaped sheath container for accommodating the radiation shield member and having an opening end, a first engaging portion formed on an outer peripheral surface thereof in the vicinity of the opening end thereof, and an inner peripheral surface;

a cup-shaped radiation shield container made of radiation shield material, having an opening end, a predetermined thickness, an outer peripheral surface of a side wall thereof which substantially contacts the inner peripheral surface of the sheath container, and a position-fixing portion, for fixing the wing-shaped holding member, to be engaged by the wing-shaped holding member at the opening end thereof;

a cup-shaped cover mounted on the opening end of the sheath container, having a cup-shaped radiation shield member made of radiation shield material and held therein, a second engaging portion which engages the first engaging portion of the sheath container, thus closing the opening of the sheath container by engagement between the first engaging portion and the second engaging portion; and a holding frame, said holding frame including:

a portion having a frame-shaped sectional configuration and a size appropriate for contacting the inner peripheral surface of the sheath container in the vicinity of the opening end thereof;

a shield container removal-preventing portion extending from the frame-shaped sectional portion toward a center of the frame-shaped sectional portion in contact with an end surface of the opening end of the radiation shield container, thus preventing the radiation shield container from being removed from the sheath container; and a shield member removal-preventing portion extending from the radiation shield container removal-preventing portion so as to cover the wing-shaped holding member engaged with the position-fixing portion for fixing the wing-shaped holding member, thus preventing the radiation shield member from being removed from the radiation shield container.

2. The transport container for accommodating the radiation shield member according to claim 1, wherein when the opening of the sheath container is closed by the cover due to the engagement between the first engaging portion and the second engaging portion, an end surface of the cup-shaped radiation shield container mounted on the cover contacts the radiation shield container removal-preventing portion and the shield member removal-preventing portion of the holding frame.

3. The transport container for accommodating the radiation shield member according to claim 2, wherein the sheath container has a third engaging portion on the inner peripheral surface thereof; and the radiation shield container has a fourth engaging portion, on the outer peripheral surface of the side wall thereof, which engages the third engaging portion, thus preventing the radiation shield container from rotating relative to the sheath container.

4. The transport container for accommodating the radiation shield member according to claim 3, wherein the cover has a fifth engaging portion on an inner peripheral surface of a side wall thereof; and the cup-shaped radiation shield member formed on the cover has a height smaller than a depth of the cover, a side wall, an outer side of which is opposed to an inner peripheral surface of a side wall of the cover with a gap provided therebetween, and on an outer peripheral surface of the side wall thereof a sixth engaging portion engaging the fifth engaging portion, thus removably holding the cup-shaped radiation shield member on the cover.

5. The transport container for accommodating the radiation shield member according to claim 4, wherein a mountain-shaped first guide projection having a slide surface is formed on an outer peripheral surface of a side wall of the sheath container in the vicinity of the opening end thereof; and an inverted mountain-shaped second guide projection having a slide surface is formed on an inner peripheral surface of a side wall of the cover, the slide surface of the first guide projection and the slide surface of the second guide projection slide in contact with each other by rotating the cover at least in its circumferential direction so as to move the cover in an axial direction of the sheath container and separate the cover from the sheath container.

6. The transport container for accommodating the radiation shield member according to claim 5, wherein when the sheath container and the cover are connected with each other to seal the transport container due to the engagement between the first engaging portion and the second engaging portion, the transport container is unsealed by tearing a sealing connection portion at a notch, formed thereon, which is thin to be easily torn and formed on an outer peripheral surface of a side wall of the cover in correspondence to the second engaging portion of the cover.

7. The transport container for accommodating the radiation shield member according to claim 2, wherein the cover has a fifth engaging portion on an inner peripheral surface of a side wall thereof; and the cup-shaped radiation shield member formed on the cover has a height smaller than a depth of the cover, a side wall, an outer side of which is opposed to an inner peripheral surface of a side wall of the cover with a gap provided therebetween, and on an outer peripheral surface of the side wall thereof a sixth engaging portion engaging the fifth engaging portion, thus removably holding the cup-shaped radiation shield member on the cover.

8. The transport container for accommodating the radiation shield member according to claim 2, wherein a mountain-shaped first guide projection having a slide surface is formed on an outer peripheral surface of a side wall of the sheath container in the vicinity of the opening end thereof; and an inverted mountain-shaped second guide projection having a slide surface is formed on an inner peripheral surface of a side wall of the cover, the slide surface of the first guide projection and the slide surface of the second guide projection slide in contact with each other by rotating the cover at least in its circumferential direction so as to move the cover in an axial direction of the sheath container and separate the cover from the sheath container.

9. The transport container for accommodating the radiation shield member according to claim 2, wherein the sheath container and the cover are connected with each other to seal the transport container due to the engagement between the first engaging portion and the second engaging portion, the transport container is unsealed by tearing a sealing connection portion at a notch, formed thereon, which is thin to be easily torn and formed on an outer peripheral surface of a side wall of the cover in correspondence to the second engaging portion of the cover.

10. The transport container for accommodating the radiation shield member according to claim 1, wherein the sheath container has a third engaging portion on the inner peripheral surface thereof; and the radiation shield container has a fourth engaging portion, on the outer peripheral surface of the side wall thereof, which engages the third engaging portion, thus preventing the radiation shield container from rotating relative to the sheath container.

11. The transport container for accommodating the radiation shield member according to claim 1, wherein the cover has a fifth engaging portion on an inner peripheral surface of a side wall thereof; and the cup-shaped radiation shield member formed on the cover has a height smaller than a depth of the cover, a side wall, an outer side of which is opposed to an inner peripheral surface of a side wall of the cover with a gap provided therebetween, and on an outer peripheral surface of the side wall thereof a sixth engaging portion engaging the fifth engaging portion, thus removably holding the cup-shaped radiation shield member on the cover.

12. The transport container for accommodating the radiation shield member according to claim 1, wherein a mountain-shaped first guide projection having a slide surface is formed on an outer peripheral surface of a side wall of the sheath container in the vicinity of the opening end thereof; and an inverted mountain-shaped second guide projection having a slide surface is formed on an inner peripheral surface of a side wall of the cover, the slide surface of the first guide projection and the slide surface of the second guide projection slide in contact with each other by rotating the cover at least in its circumferential direction so as to move the cover in an axial direction of the sheath container and separate the cover from the sheath container.

13. The transport container for accommodating the radiation shield member according to claim 1, wherein when the sheath container and the cover are connected with each other to seal the transport container due to the engagement between the first engaging portion and the second engaging portion, the transport container is unsealed by tearing a sealing connection portion at a notch, formed thereon, which is thin to be easily torn and formed on an outer peripheral surface of a side wall of the cover in correspondence to the second engaging portion of the cover.

* * * * *